United States Patent [19]

Armor et al.

[11] Patent Number: 5,756,741
[45] Date of Patent: May 26, 1998

[54] PROCESS FOR THE PRODUCTION OF TRIETHYLENEDIAMINE

[75] Inventors: John Nelson Armor, Orefield; Jose Guadalupe Santiesteban; Hong-Xin Li, both of Allentown, all of Pa.

[73] Assignee: Air Products and Chemicals, Inc., Allentown, Pa.

[21] Appl. No.: 751,142

[22] Filed: Nov. 15, 1996

[51] Int. Cl.[6] .................................................. C07D 487/08
[52] U.S. Cl. .................................. 544/352; 544/351
[58] Field of Search .................................. 540/351, 352

[56] References Cited

U.S. PATENT DOCUMENTS

| | | | |
|---|---|---|---|
| 3,956,329 | 5/1976 | Murakami et al. | 260/268 SY |
| 4,405,784 | 9/1983 | Wells et al. | 544/352 |
| 4,804,758 | 2/1989 | Hoelderich et al. | 544/325 |
| 4,966,969 | 10/1990 | Sato et al. | 544/352 |
| 5,037,838 | 8/1991 | Zimmerman et al. | 544/352 |
| 5,041,548 | 8/1991 | Sato et al. | 544/352 |
| 5,162,531 | 11/1992 | King | 544/352 |

FOREIGN PATENT DOCUMENTS

| | | |
|---|---|---|
| 0158319 | 10/1985 | European Pat. Off. . |
| 0313753 | 5/1989 | European Pat. Off. . |
| 0312734 | 1/1992 | European Pat. Off. . |
| 0423526 | 11/1993 | European Pat. Off. . |

OTHER PUBLICATIONS

Translation of AP 382055 (1990).

*Primary Examiner*—Mark L. Berch
*Attorney, Agent, or Firm*—Michael Leach

[57] ABSTRACT

A process for preparing triethylenediamine by passing an amine compound over a catalyst at elevated temperature to afford a reaction product containing triethylenediamine and piperazine, the amine compound having, in the molecule, a moiety represented by the following general formula

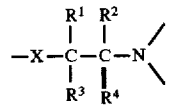

where $R^1$, $R^2$, $R^3$ and $R^4$ are independently a hydrogen atom or an alkyl group having 1 to 4 carbon atoms and X is oxygen or nitrogen characterized by adding an ethylating compound containing at least one nitrogen and/or oxygen atom to the reaction product and contacting the reaction product, under conditions sufficient to produce triethylenediamine from the ethylating compound and piperazine, with a condensation/cyclization shape-selective zeolite catalyst demonstrating a triethylenediamine/piperazine weight ratio uptake value of at least 6:1.

13 Claims, No Drawings

PROCESS FOR THE PRODUCTION OF TRIETHYLENEDIAMINE

CROSS REFERENCE TO RELATED APPLICATION

Not applicable.

STATEMENT REGARDING FEDERALLY SPONSORED RESEARCH OR DEVELOPMENT

Not applicable.

BACKGROUND OF THE INVENTION

The present invention relates a process for preparing triethylenediamine (TEDA) by contacting nitrogen-containing compounds with zeolites at elevated temperature.

The synthesis of TEDA from a variety of amine compounds using metallosilicates, mixed metal oxides and phosphate catalysts is well known in the art.

U.S. Pat. No. 3,956,329 discloses a process for preparing TEDA from a number of amine compounds using zeolite catalysts with a $SiO_2/Al_2O_3$ (silica to alumina) ratio between 2 and 12.

U.S. Pat. No. 4,804,758 discloses the preparation of TEDA from certain heterocyclic amines in the presence of borosilicate and/or iron silicate zeolites as catalysts.

U.S. Pat. Nos. 4,966,969 and 5,041,548 disclose the preparation of TEDA from amine compounds using a catalyst comprising a crystalline metallosilicate having a silica/metal oxide molar ratio of 12/1 or more, in particular, a metallosilicate crystallized in the presence of an organic crystallizing agent.

EP 158 319 discloses a method of preparing TEDA by contacting acyclic or heterocyclic amines with high-silica zeolite having a silica to alumina ratio of at least 20 to 1.

EP 382 055 discloses a process for synthesizing TEDA from ethylenediamine and 0 to 200 mole % piperazine on aluminum, boron, gallium and/or iron silicate zeolites.

EP 423 526 discloses the preparation of TEDA and piperazine from ethylenediamine-water mixtures which is catalyzed by zeolites of the pentasil type with weakened acidity, i.e., which contain alkali metal ions or in which the aluminum of the zeolite skeleton has been isomorphously replaced by iron.

EP 312 734 discloses that piperazine can be converted directly to TEDA in the presence of zeolites, preferably zeolites having a pentasil, especially a ZSM-5, structure.

EP 313 753 discloses the preparation of mixtures of TEDA and piperazine from polyethylene polyamines and/or ethanolamines using a pentasil zeolite.

U.S. Pat. No. 5,037,838 discloses a continuous process for the manufacture of TEDA from N-hydroxyethylpiperazine by passing such feedstock over a bed of catalyst in a reaction zone wherein the catalyst is composed of pellets of a titania-supported tungstopyrophosphate catalyst.

U.S. Pat. No. 4,405,784 discloses SrHPO4 as a catalyst for making TEDA.

U.S. Pat. No. 5,162,531 discloses mixed metal oxides for producing TEDA.

Thus the pentasil-type zeolites as well as other catalysts can be used to produce TEDA in relatively high yields from a variety of polyamine feedstocks. However, significant amounts of piperazine (PIP) are also formed, e.g., the reactor effluent may contain TEDA and PIP in a molar ratio of 1 to 1.5. The PIP by-product may need to be separated from the TEDA and recycled in order to maximize TEDA production.

BRIEF SUMMARY OF THE INVENTION

The present invention is directed to an improvement in the known processes for preparing triethylenediamine (TEDA) by contacting an amine-containing compound with a catalyst at elevated temperatures to yield a reaction product comprising TEDA and piperazine (PIP). According to the invention an ethylating compound containing at least one nitrogen and/or oxygen atom is added to the TEDA- and PIP-containing reaction product which is contacted with a condensation/cyclization shape-selective zeolite catalyst under conditions sufficient to produce TEDA from the ethylating compound and PIP.

Thus, there is provided a process for maximizing the production of TEDA from amino-containing compounds which comprises the steps of: (1) charging a feed comprising amino-containing compounds to a first catalyst-containing reaction zone under conditions sufficient to produce an effluent product comprising TEDA and PIP; and (2) reacting both the effluent product from the first reaction zone and an ethylating compound containing at least one nitrogen and/or oxygen atom in a second reaction zone wherein PIP and the ethylating compound are contacted with a condensation/cyclization shape-selective zeolite-based catalyst under conditions sufficient to react the ethylating compound and PIP to produce TEDA.

As an advantage of the invention, recycle of PIP can be minimized or eliminated by having a second reaction zone in which PIP selectively can be further reacted with a C2 compound, e.g., monoethanolamine (MELA), to give TEDA. The catalyst to be used in the second reaction zone is a shape-selective catalyst that selectively catalyzes the reaction between the smaller molecules (PIP and the ethylating compound) and essentially prevents TEDA, produced in the first reaction zone, from further reacting.

BRIEF DESCRIPTION OF THE SEVERAL VIEWS OF THE DRAWINGS

Not applicable.

DETAILED DESCRIPTION OF THE INVENTION

As the starting material to be used in the process for preparing TEDA, any amine compound having, in the molecule, a moiety represented by the following general formula can be used:

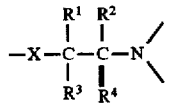

where $R^1$, $R^2$, $R^3$ and $R^4$ are independently a hydrogen atom or an alkyl group having 1 to 4 carbon atoms and X is oxygen or nitrogen. Typical examples of suitable amine compounds are ethanolamines, including monoethanolamine, diethanolamine and triethanolamine; isopropanolamines, including monoisopropanolamine and diisopropanolamine; ethyleneamines, including ethylenediamine, diethylenetriamine and triethylenetetramine; piperazine and its derivatives N-hydroxyethylpiperazine and N-aminoethylpiperazine; morpholine and obviously mixtures of the foregoing.

Any of the catalysts well known in the art for producing TEDA from the amine compounds can be used in the first reaction stage, e.g., phosphate-containing catalysts such as $SrHPO_4$ or a pentasil-type zeolite in the hydrogen (H+) and/or ammonium ($NH_4$+) form. The TEDA producing reaction is conducted under conditions also well known in the art as evidenced by above cited patent documents.

The catalyst in the first reaction zone, for example, can be an aluminosilicate zeolite, preferably of the pentasil type such as ZSM-5, having a silica/alumina ratio greater than 20. These zeolite catalysts may be modified to improve their catalytic properties with techniques such as steaming and chemical treatment with inorganic and/or organic compounds.

Other type of catalysts that can be used in the first reaction zone are phosphate-containing catalysts such as phosphates of Sr, Ca, Al, and the like, and also mixed metal oxide catalysts as described in U.S. Pat. No. 5,162,531. The phosphate-containing catalysts, in particular, $SrHPO_4$, is expected to be useful when using feedstocks containing appreciable amounts of piperazine and hydroxyethylpiperazine.

The reaction conditions in the first zone should be such as to cause condensation and/or cyclization reactions that give rise to formation of cyclic amines such as TEDA and piperazine. The first zone reaction can be carried out at temperatures of less than 450° C., for example 200° to 400° C., preferably between 300° and 400° C., pressures ranging from about 0.001 to 200 atm (0.1 to 20,000 kPa), preferably between about 0.01 and 10 atm (1 to 1000 kPa), and weight hourly space velocities (WHSV) based on amine feedstocks between 0.01 and 10 $hr^{-1}$, preferably between 0.1 and 2 $hr^{-1}$. The preferred process variables depend upon the rate of reaction desired to produce TEDA.

The reaction can be performed batch-wise, semi-continuously or continuously. In the case of the continuous reaction, the WHSV (weight hourly space velocity) usually ranges from 0.01 to 10 $hr^{-1}$. The preferred WHSV is determined depending on the temperature. For example, at 300° C., WHSV is 0.02 to 2 $hr^{-1}$, and at 350° C., it is 0.1 to 5 $hr^{-1}$.

In the reaction of the amine compound as a starting material, it may be diluted with an inert gas such as hydrogen, nitrogen, steam or hydrocarbons, or with an inert solvent such as water and inert hydrocarbons. By using these diluents, the reaction can be controlled appropriately.

The feedstock for the second reaction zone contains the product effluent from the first reaction zone along with interstage feeding of an oxygen and/or nitrogen containing ethylating compound, for example, an ethylenediamine including polyethylenepolyamines such as diethylenetriamine, alkylamine compound(s) containing oxygen atom(s), including ethanolamines such as monoethanolamine, and oxygenate compounds, such as ethylene glycol, containing no nitrogen atoms.

The reaction conditions in the second reaction zone may be similar to those used in the first reaction zone or may be different, depending on feed composition and catalyst used in the first reaction zone, to optimize TEDA production rate. The second reaction can also be performed batch-wise, semi-continuously or continuously as described above for the first reaction.

The catalyst of the second reaction zone is a shape-selective catalyst of the pentasil type, for example, ZSM-5, having a silica to alumina ratio greater than 20. The pore dimensions of this type of zeolite (5.1×5.5 Å, 5.3×5.6 Å) enable one to selectively catalyze the reaction between smaller molecules, for example PIP and interstage co-fed MELA, to produce TEDA. The pore dimensions of ZSM-5 are such that the TEDA molecule produced in the first stage is essentially excluded from entering the pores, thus, preventing TEDA from decomposing into undesired by-products. This type of shape selectivity, which is taking place in the second reaction zone of the process of this invention, is based on the principle of molecular exclusion, and is known as reactant selectivity. See "Molecular Transport and Reaction in Zeolites," by N. Y. Chen, T. F. Degnan, and C. M. Smith, 1994 VCH Publishers, Inc., N.Y., p. 174.

The shape-selective crystalline metallosilicate (zeolite) used as the catalyst in the second reaction zone has a crystal skeleton mainly comprised of silicon dioxide (silica; $SiO_2$) and a metal oxide such as aluminum oxide (alumina; $Al_2O_3$), iron oxide or boron oxide. Alumina is the preferred metal oxide. The silica/metal oxide molar ratio is 20:1 or more, preferably 25:1 to 1000:1, and more preferably 50:1 to 500:1.

The particular zeolite catalysts useful for the second reaction zone of this process can be distinguished from other zeolites by their uptake characteristics of, for example, PIP/TEDA mixtures. Tables 1 and 2 compare the uptake results obtained for ZSM-5 and Beta zeolites, respectively. Uptake results obtained for ZSM-5 in Table 1 clearly show that PIP uptake more readily occurred than TEDA uptake. On the other hand, results obtained for the larger pore Beta zeolite (6.4×7.6 Å, 5.5×5.5 Å) revealed that both TEDA and PIP uptake occurred at comparable rates with the TEDA uptake being over 90%. The uptake experiments consisted in adding the respective zeolite material to an aqueous solution containing known amounts of PIP and TEDA. The uptake of the amines by the zeolites was determined by following the concentration of amines in the solution by gas chromatography. Samples from the solution were taken with a microsyringe.

TABLE 1

| TIME (min) | Piperazine Uptake[a] | TEDA Uptake[b] |
| --- | --- | --- |
| 0 | 0 | 0 |
| 210 | 85.4 | 4.7 |
| 1140 | 95.7 | 13.5 |
| 2580 | 96.1 | 15.1 |
| 4500 | 96.3 | 10.0 |

[a]Amount (wt %) of piperazine adsorbed from the solution by ZSM-5.
[b]Amount (wt %) of TEDA adsorbed from the solution by ZSM-5.

TABLE 2

| TIME (min) | Piperazine Uptake[a] | TEDA Uptake[b] |
| --- | --- | --- |
| 5 | 93.1 | 68.9 |
| 15 | 100 | 91.7 |
| 45 | 100 | 97.3 |

[a]Amount (wt %) of piperazine adsorbed from the solution by Beta zeolite.
[b]Amount (wt %) of TEDA adsorbed from the solution by Beta zeolite Thus suitable shape selective zeolites would be those demonstrating a PIP/TEDA relative weight ratio uptake of at least 6:1, preferable at least 15:1, as determined by gas chromatographic analysis of a sample from 10 mL of an aqueous solution of 0.5 wt % PIP and 1.0 wt % TEDA contacted with 2 g zeolite at 25° C. for 200 min. From Table 1 it can be seen that ZSM-5 zeolite demonstrates a PIP/TEDA weight ratio uptake value of about 18 at about 200 min.

To further demonstrate the inability of TEDA to get into the pore system of ZSM-5, an aqueous solution of 10 wt % TEDA was fed into a reactor containing ZSM-5 catalyst at 340° C., atmospheric pressure, WHSV (based on TEDA) of 0.1 $hr^{-1}$, and co-feeding nitrogen at GHSV of 480 $hr^{-1}$. The results indicated that only a very small decomposition of TEDA, ~2%, took place. Similar experiments using a larger pore Y zeolite (pore diameter about 7.4 Å) revealed a 51% decomposition of TEDA.

There are no special limitations to the crystalline aluminosilicate that is used in the second reaction zone as long as it satisfies the above PIP/TEDA uptake value and optionally, but advantageously, the silica/alumina molar ratio of >20:1. Crystalline aluminosilicates having a main pore made of a ten-member ring of oxygen, especially those belonging to members of the pentasil-type structure, are preferred with ZSM-5 zeolite being most preferred.

The preparation of suitable pentasil zeolite catalysts is well known to those skilled in the art as illustrated by the previously cited references. In addition, suitable pentasil zeolites are commercially available from many sources such as Degussa AG and CU Chemie Uetikon AG.

Crystalline aluminosilicates of the pentasil family as obtained by the hydrothermal synthesis using an organic crystallizing agent are particularly preferred. Among the pentasil types, the zeolite structures ZSM-5, ZSM-11, ZSM-8, and ZSM-5/ZSM-11-intermediates are preferred, especially ZSM-5.

The zeolite catalysts are used in their hydrogen form (H+) and/or their ammonium form ($NH_4+$).

For example, a pentasil-type crystalline aluminosilicate can be prepared by the hydrothermal synthesis using a mixture composed mainly of a silica source, e.g., colloidal silica, silica gel, or silicic acid salts such as water glass, and an aluminum oxide source, e.g., the sulfuric acid salts, nitric acid salts or oxy acid salts of alumina, such as aluminum sulfate and sodium aluminate, in the absence or preferably in the presence of an organic crystallizing agent, e.g., amines such as tetraalkylammonium halide having 2 to 5 carbon atoms.

There is also known a method in which the hydrothermal synthesis is performed in the presence of alkali metal compounds such as the hydroxides and halides of alkali metal such as sodium and the like.

The crystalline aluminosilicate obtained by these methods is generally not of the H+ or $NH_4+$ form, but of the form that H+ and $NH_4+$ are replaced by quaternary ammonium ion and/or alkali metal ion such as Na+ and the like. Therefore, the crystalline aluminosilicate must be changed into the H+ or $NH_4+$ form, and this exchange can be easily achieved by known methods.

For changing the alkali metal ion zeolite into H+ or $NH_4+$, there is often employed a method in which the alkali metal salt-type crystalline aluminosilicate is treated with an aqueous solution of ammonium salts, such as ammonium nitrate and ammonium sulfate, to form an ammonium salt-type crystalline aluminosilicate. The ammonium salt-type crystalline aluminosilicate may then be calcined in the air at a temperature of 300° to 600° C., preferably 400° to 500° C., to obtain the H+ form crystalline zeolite.

While the zeolite used in the second stage reaction zone is preferably of the H+ and/or $NH_4+$ form, the H+ and/or $NH_4+$ may be partially replaced by other cations, such as alkali, alkaline earth, rare earth, transition metals, oxides etc., as long as the object of the present invention can be obtained.

The catalyst of the second reaction zone can be used in any desired form, such as powder, particles, strips, spheres and pellets. The catalyst can be self-bound or molded with a binder such as silica, alumina, titania, zirconia, natural clays and/or mixtures of these materials be mixed with the zeolite. Naturally occurring clays which can be composited with the zeolite catalyst include the montmorillonite and kaolin family. These clays can be used in the raw state as originally mined or initially subjected to calcination, acid treatment or chemical modification.

Of all the matrix materials mentioned above, materials of low acidity such as silica or zirconia are preferred in that they prevent unwanted side reactions engendered by more active materials such as alumina. The performance of alumina can, however, be improved by altering its acid properties via chemical modification.

The relative proportions of zeolite and matrix material can vary widely with the zeolite content ranging from 10 to 98 wt %, and more usually in the range of 50 to 90 wt %, of the composite.

Thus in accordance with the process of the present invention, the desired TEDA can be efficiently obtained by reacting in a first reaction zone an amine compound having in the molecule a moiety represented by the general formula:

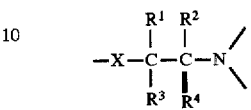

or preferably the general formula:

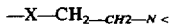

where $R^1$, $R^2$, $R^3$ and $R^4$ are independently a hydrogen atom or an alkyl group having 1 to 4 carbon atoms and X is nitrogen or oxygen as the starting material using a catalyst to afford a TEDA- and PIP-containing reaction product followed by adding an ethylating compound to the reaction product and contacting with a shape-selective zeolite having a PIP/TEDA weight ratio uptake value of at least 6:1.

The reactions of the amine compound in the first stage and the ethylating compound-containing first reaction product in the second stage proceed on contacting them with the described catalysts under pressures ranging from 0.001 to 200 atm (0.1 to 20,000 kPa), preferably 0.01 to 10 atm (1 to 1000 kPa). Reaction conditions, such as reaction temperature, reaction time and starting materials/catalyst ratio, for both the first and second reaction zones cannot be determined unconditionally because they vary with the type of amine compound, the type of zeolite catalyst, reaction pressure and the like. Usually the reaction temperature is chosen within the range 100° to 450° C., preferably 300° to 400° C.

The ethylating agent can be added directly into the TEDA- and PIP-containing effluent from the first reaction zone or separately charged into the second reaction zone. Also, it is possible to use a single reaction vessel having two reaction zones in series, or stages, wherein interstage feeding of the ethylating agent is performed. Thus, one reaction vessel contains the same catalyst but is divided into two zones. The amine compound is charged into the first zone and as the reaction product proceeds to the second zone, the ethylating agent is added. In such a case, the reaction conditions may be the same throughout.

The following examples illustrate the reaction taking place in the second reaction zone of the inventive process, i.e., MELA-PIP over ZSM-5 to produce TEDA.

EXAMPLE 1

TEDA synthesis from an aqueous solution containing 7.4 wt % MELA/12.8 wt % piperazine/79.8 wt % H2O was carried out over ZSM-5 (obtained from CU Chemie Uetikon AG ZEOCAT PZ 2/250, $SiO_2/Al_2O_3$ molar ratio of 250; H+ form) in a plug-flow reactor at atmospheric pressure and 350° C. The aqueous solution flow rate, expressed as WHSV (g organic feed/g zeolite/hr) was 0.2 $hr^{-1}$. Nitrogen was co-fed to the reactor at GHSV of 250 $hr^{-1}$. The results are shown in Table 3.

EXAMPLE 2

This example describes the results obtained over a ZSM-5 catalyst (obtained from Süd Chemie, $SiO_2/Al_2O_3$ molar ratio of 90; H+ form). Organic feed composition was 6.1 wt % MELA/10.7 wt % PIP/83.2 wt % H2O. The operating conditions were: 350° C., atmospheric pressure, WHSV (g organic feed/g zeolite/hr) of 0.2 hr$^{-1}$, nitrogen was co-fed to the reactor at GHSV 500 hr$^{-1}$. The results are shown in Table 3.

TABLE 3

| Ex | WHSV$_{(org)}$ hr$^{-1}$ | MELA Conv (wt %) | PIP Conv (wt %) | TEDA Selectivity (mole %) |
|---|---|---|---|---|
| 1 | 0.2 | 73 | 77 | 68 |
| 2 | 0.2 | 95 | 74 | 90 |

As can be seen from the data in Table 3 the process of this invention minimizes or eliminates the need to recycle piperazine or other unreacted amines by having two reaction zones, wherein the second reaction zone contains a shape-selective ZSM-5 zeolite to eclude TEDA produced in the first zone from further reacting, while reacting the smaller amino compounds MELA and PIP to form TEDA.

EXAMPLE 3

The catalyst used was the same as in Example 2. Ethylenediamine (EDA) was the ethylating agent. The organic feed composition was 17.5 wt % EDA/7.5 wt % PIP/75 wt % H$_2$O. The reaction was carried out at 340° C., atmospheric pressure, WHSV (g organic feed/g catalyst/hr) of 0.29 hr–$^1$, nitrogen co-fed at GHSV 1800 hr–$^1$. The results in Table 4 show that PIP from a first reaction zone could be reacted with an ethylating agent over shape-selective ZSM-5 zeolite to afford TEDA, avoiding recycling of the PIP.

TABLE 4

| Ex | WHSV$_{(org)}$ hr–$^1$ | EDA Conv (wt %) | PIP Conv (wt %) | TEDA Selectivity (mole %) |
|---|---|---|---|---|
| 3 | 0.29 | 100 | 41 | 92 |

EXAMPLE 4

This example was performed with a TEDA-containing PIP/MELA feed to illustrate that TEDA present in the feed to the second reaction zone essentially does not decompose at operating conditions at which PIP and MELA react to produce more TEDA. The reaction was performed using a ZSM-5 catalyst (obtained from Süd Chemie, SiO$_2$/Al$_2$O$_3$ molar ratio of 90). The organic feed composition was 24.8 wt % TEDA/10.9 wt % PIP/6.0 wt % MELA/58.3 wt % H2O. The operating conditions were; 350° C., atmospheric pressure, WHSV (g organic feed/g catalyst/hr) of 0.6 hr–$^1$, nitrogen was co-fed to the reactor at GHSV 1250 hr–$^1$. The results are shown in Table 5 and demonstrate that adding the ethylating agent MELA to a mixture of PIP and TEDA and reacting over ZSM-5 catalyst produced additional TEDA from MELA and PIP.

TABLE 5

| Compound | Feed (wt %) | Product (wt %) | Conv (wt %) | TEDA Sel[a] (mole %) |
|---|---|---|---|---|
| MELA | 6.0 | 0 | 100 | — |
| PIP | 10.9 | 4.9 | 55 | — |
| TEDA | 24.8 | 32.8 | — | 90 |
| Others[b] | 0 | 1.6 | — | — |
| Total | 41.7 | 39.3 | — | — |

[a]Selectivity of TEDA produced from MELA and PIP
[b]Mainly ethylpiperazine

INDUSTRIAL APPLICATION

The present invention provides a combined process, consisting of at least two reaction zones, to maximize TEDA production.

We claim:

1. A process for the production of triethylenediamine from an amino-containing compound which comprises the steps of: (1) charging a feed comprising an amino-containing compound which is monoethanolamine, diethanolamine, triethanolamine, ethylenediamine, diethylenetriamine, triethylenetetramine, piperazine, N-hydroxyethyl-piperazine, N-aminoethylpiperazine; morpholine or a mixture thereof to a first catalyst-containing reaction zone under conditions sufficient to produce an effluent product comprising triethylenediamine and piperazine; (2) adding to the effluent product from the first reaction zone an ethylating compound which is ethylenediamine, a polyethylenepolyamine, an ethanolamine, ethylene glycol or a mixture thereof and (3) reacting the effluent product from the first rdaction zone and the added ethylating compound in a second reaction zone wherein piperazine and the ethylating compound are contacted with a condensation/cyclization shape-selective zeolite catalyst having a silica/alumina molar ratio of >20:1 under conditions sufficient to react the ethylating compound and piperazine to produce triethylenediamine.

2. The process of claim 1 in which the zeolite catalyst has a piperazine/triethylenediamine weight ratio uptake value of at least 6:1, as determined by gas chromatographic analysis of a sample from 10 mL of an aqueous solution of 0.5 wt % piperazine and 1.0 wt % triethylenediamine contacted with 2 g zeolite at 25° C. for 200 min.

3. The process of claim 1 in which the zeolite is a ZSM-5, ZSM-8 or ZSM-11 zeolite in the hydrogen (H+) and/or ammonium (NH$_4$+) form.

4. The process of claim 3 in which the zeolite has a silica/alumina molar ratio of 25:1 to 1000:1.

5. The process of claim 4 in which the amine compound is monoethanolamine, ethylenediamine, diethylenetriamine, piperazine or a mixture thereof.

6. The process of claim 5 in which the ethylating compound is monoethanolamine or ethylenediamine.

7. The process of claim 6 in which the zeolite is ZSM-5.

8. The process of claim 2 in which the zeolite catalyst has a piperazine/triethyleneodiamine weight ratio uptake value of at least 15:1.

9. The process of claim 8 in which the zeolite is a ZSM-5, ZSM-8 or ZSM-11 zeolite in the hydrogen (H+) and/or ammonium (NH$_4$+) form.

10. The process of claim 9 in which the zeolite has a silica/alumina molar ratio of 25:1 to 1000:1.

11. The process of claim 10 in which the amine compound is monoethanolamine, ethylenediamine, diethylenetriamine, piperazine or a mixture thereof.

12. The process of claim 11 in which the ethylating compound is monoethanolamine or ethylenediamine.

13. The process of claim 12 in which the zeolite is ZSM-5.

* * * * *